United States Patent
Jencks et al.

(10) Patent No.: US 10,254,255 B2
(45) Date of Patent: Apr. 9, 2019

(54) ROTARY SELECTOR VALVE AND ASSOCIATED SYSTEMS AND METHODS

(71) Applicant: Waters Technologies Corporation, Milford, MA (US)

(72) Inventors: Robert A. Jencks, Mendon, MA (US); Mark W. Moeller, Kingston, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 557 days.

(21) Appl. No.: 14/429,529

(22) PCT Filed: Sep. 18, 2013

(86) PCT No.: PCT/US2013/060291
§ 371 (c)(1),
(2) Date: Mar. 19, 2015

(87) PCT Pub. No.: WO2014/047108
PCT Pub. Date: Mar. 27, 2014

(65) Prior Publication Data
US 2015/0226712 A1    Aug. 13, 2015

Related U.S. Application Data

(60) Provisional application No. 61/703,485, filed on Sep. 20, 2012.

(51) Int. Cl.
*G01N 30/34* (2006.01)
*G01N 30/36* (2006.01)
(Continued)

(52) U.S. Cl.
CPC .............. *G01N 30/36* (2013.01); *F16K 11/07* (2013.01); *F16K 11/0743* (2013.01);
(Continued)

(58) Field of Classification Search
CPC ........ G01N 30/36; G01N 30/34; F16K 11/07; F16K 11/0743; Y10T 137/86541; Y10T 137/0318
See application file for complete search history.

(56) References Cited

U.S. PATENT DOCUMENTS 3,985,021 A * 10/1976 Achener ................. G01N 30/34
210/198.2
4,437,812 A * 3/1984 Abu-Shumays ..... B01D 15/166
210/198.2
(Continued)

FOREIGN PATENT DOCUMENTS

WO    2011130071 A1    10/2011

*Primary Examiner* — Craig Schneider
*Assistant Examiner* — Frederick D Soski
(74) *Attorney, Agent, or Firm* — Womble Bond Dickinson (US) LLP; Deborah M. Vernon; Heath T. Misley

(57) ABSTRACT

Exemplary embodiments are directed to a rotary selector valve that includes a valve body that includes a rotor and a stator. The stator includes a first port for flow of a first flow material and a second port for flow of a second flow material. The rotor includes a groove for flow of at least one of the first flow material and the second flow material. The rotor includes a vent groove disposed between the first port and the second port for venting at least a portion of at least one of the first flow material and the second flow material to an exterior of the valve body. Exemplary methods of operating a rotary selector valve and CO2-based chromatography flow systems including a rotary selector valve are also provided.

11 Claims, 13 Drawing Sheets

(51) Int. Cl.
 *F16K 11/07* (2006.01)
 *F16K 11/074* (2006.01)
(52) U.S. Cl.
 CPC ......... *G01N 30/34* (2013.01); *Y10T 137/0318* (2015.04); *Y10T 137/86541* (2015.04)

(56) References Cited

U.S. PATENT DOCUMENTS

| | | | |
|---|---|---|---|
| 4,702,889 A | | 10/1987 | Cabrera et al. |
| 5,080,785 A | * | 1/1992 | Allington ............... G01N 30/34 210/101 |
| 5,193,581 A | * | 3/1993 | Shiroto ............... F16K 11/0743 137/312 |
| 6,012,488 A | * | 1/2000 | Nichols ............... F16K 11/0743 137/625.11 |
| 6,428,702 B1 | | 8/2002 | Berger et al. |
| 2002/0116989 A1 | * | 8/2002 | Davison ................ B01D 15/12 73/61.55 |
| 2005/0121392 A1 | * | 6/2005 | Hoffman ............. B01D 15/166 210/656 |
| 2006/0042686 A1 | | 3/2006 | Gamache et al. |
| 2013/0015138 A1 | * | 1/2013 | Schlake ............... B01D 15/165 210/656 |

\* cited by examiner

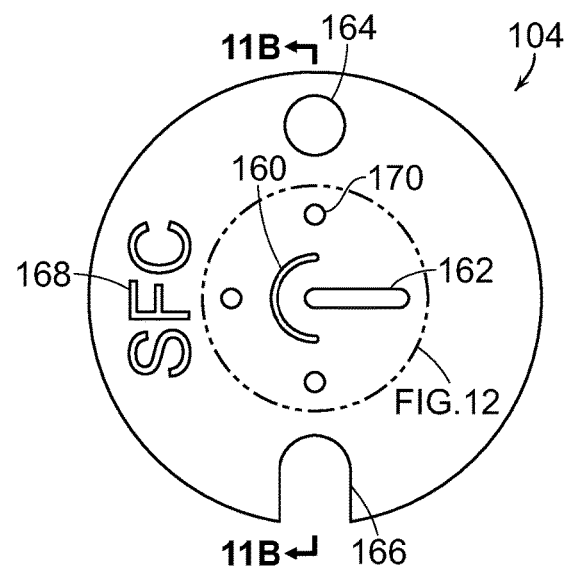
FIG. 11A
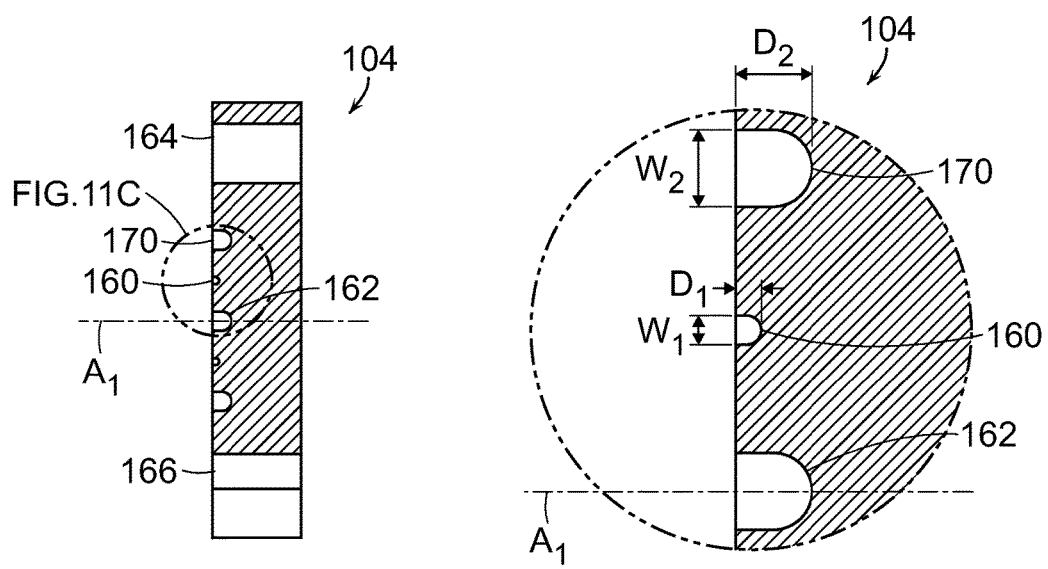
FIG. 11B
FIG. 11C

ROTARY SELECTOR VALVE AND ASSOCIATED SYSTEMS AND METHODS

RELATED APPLICATIONS

This application is a National Stage Application of International Application No. PCT/US2013/060291, filed Sep. 18, 2013, which claims priority to U.S. Provisional Application No. 61/703,485, filed Sep. 20, 2012. Each of the foregoing applications is incorporated herein by reference in its entirety.

TECHNICAL FIELD

The present disclosure relates to rotary selector valves and associated systems and methods and, in particular, to rotary selector valves that include a vent groove for venting a flow material.

BACKGROUND

Chromatographic techniques are important tools for the identification and separation of complex samples. The basic principle underlying chromatographic techniques is the separation of a mixture into individual components by transporting the mixture in a moving fluid through a retentive media. The moving fluid is typically referred to as the mobile phase and the retentive media is typically referred to as the stationary phase. The separation of the various constituents of the mixture is based on differential partitioning between the mobile and stationary phases. Differences in components' partition coefficient result in differential retention on the stationary phase, resulting in separation.

Conventionally, the methods of choice for chromatographic separations have been gas chromatography (GC) and liquid chromatography (LC). One major difference between GC and LC is that the mobile phase in GC is a gas, whereas the mobile phase in LC is a liquid. For example, in GC, a supply of inert carrier gas (mobile phase) is continually passed as a stream through a heated column containing porous sorptive media (stationary phase). A sample of the subject mixture is injected into the mobile phase stream and passed through the column, where separation of the mixture is primarily due to the differences in the volatile characteristics of each sample component at the temperature of the column. A detector, positioned at the outlet end of the column, detects each of the separated components as they exit the column. Although GC is typically a sensitive method of analysis, the high temperatures required in GC make this method unsuitable for high molecular weight biopolymers or proteins (heat will denature them), frequently encountered in biochemistry.

Conversely, LC is a separation technique in which the mobile phase is a liquid and does not require volatilization of the sample. Liquid chromatography that generally utilizes small packing particles and moderately high pressure is referred to as high-performance liquid chromatography (HPLC); whereas liquid chromatography that generally utilizes very small packing particles and high pressure is referred to as ultra-high performance liquid or ultra-high pressure liquid chromatography (UHPLC). In HPLC and UHPLC the sample is forced by a liquid at high pressure (the mobile phase) through a column that is packed with a stationary phase composed of irregularly or spherically shaped particles, e.g., a porous monolithic layer, or a porous membrane.

Because LC uses liquid as the mobile phase, LC techniques are capable of analyzing higher molecular weight compounds and, in some cases, LC can be used to prepare large scale batches of purified protein(s). However, in contrast, GC techniques are typically more sensitive and readily allow for the separation of single chiral materials. Thus, GC has conventionally been used to isolate and determine the relative purity of a chiral compound, e.g., by determining the enantiomeric excess (% ee) or the diastereomeric excess (% de) of a particular sample. As with most chromatographic techniques, the limiting factor in both GC and LC has been the ability to obtain and/or reproduce pure sample separations, each of which are typically dependent on the apparatus, methods, and conditions employed, e.g., flow rate, column size, column packing material, solvent gradient, and the like.

Supercritical Fluid Chromatography (SFC) is another chromatographic technique, which has typically been used in preparative applications. For every liquid substance there is a temperature above which it can no longer exist as a liquid, no matter how much pressure is applied Likewise, there is a pressure above which the substance can no longer exist as a gas no matter how much the temperature is raised. These points are called the supercritical temperature and supercritical pressure, and define the boundaries on a phase diagram for a pure substance (FIG. 1). At this point, the liquid and vapor have the same density and the fluid cannot be liquefied by increasing the pressure. Above this point, where no phase change occurs, the substance acts as a supercritical fluid (SF). Thus, SF can be described as a fluid obtained by heating above the critical temperature and compressing above the critical pressure. There is a continuous transition from liquid to SF by increasing temperature at constant pressure or from gas to SF by increasing pressure at constant temperature.

The term SFC, while typically standing for Supercritical Fluid Chromatography, does not require or mean that supercritical conditions are obtained during or maintained throughout the separation. That is, columns do not have to be always operated in the critical region of the mobile phase. For example, in the event that the mobile phase includes a modifier (e.g., $CO_2$ and methanol as a modifier), the mobile phase is often in its subcritical region (e.g., a highly compressed gas or a compressible liquid rather than a supercritical fluid). In fact, as Guiochon et al note in section 2.3 of their review article entitled "Fundamental challenges and opportunities for preparative supercritical fluid chromatography" Journal of Chromatography A, 1218 (2011) 1037-1114: "It is obvious that SFC has very often been and still is run under subcritical conditions." Thus, the term SFC is not limited to processes requiring supercritical conditions.

In certain embodiments, SFC systems use $CO_2$, thereby permitting SFC processes to be inexpensive, innocuous, eco-friendly, and non-toxic. There is typically no need for the use of volatile solvent(s) (e.g., hexane). Finally, the mobile phase in SFC processes (e.g., $CO_2$ together with any modifier/additive as a SF, highly compressed gas, or compressible liquid) typically have higher diffusion constants and lower viscosities relative to liquid solvents. The low viscosity means that pressure drops across the column for a given flow rate is greatly reduced. The increased diffusivity means longer column length can be used.

Chromatographic processes using a mobile phase consisting at least in part of $CO_2$ is sometimes referred to as $CO_2$-based chromatography. $CO_2$-based chromatography can utilize supercritical or near supercritical $CO_2$ for a mobile phase. However, $CO_2$-based chromatography does not require the use of SFs. In general, $CO_2$ when used as a constituent of a mobile phase in chromatography is considered to be a compressible fluid, providing a higher diffusion constant and lower viscosity compared to liquid solvents used in LC or HPLC processes.

SUMMARY

Exemplary embodiments of the present technology include rotary selector valves and associated systems and methods which provide complete or substantially complete control of flow materials, including a vent groove for venting a flow material during potential leakage from the rotary selector valve in a $CO_2$-based chromatography system.

In general, embodiments of the present disclosure are directed to rotary selector valves that permit switching between a plurality of ports while preventing leakage of $CO_2$ into or through undesired flow paths (e.g., into a flow path leading to a methanol reservoir). In addition, embodiments of the present disclosure are directed to methods of permitting switching between a plurality of ports while preventing leakage of a highly pressurized material into a flow line designated for much lower pressures (e.g., difference of over 500 psi).

In accordance with embodiments of the present disclosure, exemplary rotary selector valves are provided that generally include a valve body that includes a rotor and a stator. The stator includes a first port for flow of a first flow material and a second port for flow of a second flow material. The rotor includes a groove, e.g., a port, slot, or any type of opening, for flow of at least one of the first flow material and the second flow material. The rotor generally includes a vent groove disposed between the first port and the second port for venting at least a portion of at least one of the first flow material and the second flow material to an exterior of the valve body.

The vent groove generally prevents at least one of flow of the first flow material into the second port and flow of the second flow material into the first port. The vent groove can be configured as, e.g., substantially C-shaped, and the like. In some exemplary embodiments, the vent groove can be configured as a C-shaped groove. The rotor and stator can be configured and dimensioned to mechanically communicate, i.e., to rotate relative to each other. The first flow material can be, e.g., $CO_2$, a solvent, and the like. The second flow material can be a modifier, e.g., methanol, ethanol, and the like.

The rotor can be manufactured from at least one of, e.g., polyether ether ketone (PEEK), polytrifluorochloroethylene (PCTFE), polyimide, ultra-high-molecular-weight polyethylene (UHMWPE), polytetrafluoroethylene (PTFE), and the like. The polytrifluorochloroethylene can be, e.g., a polymer associated with U.S. registered trade name Kel-F® of 3M Corporation of St. Paul, Minn., or a polymer sold in connection with the trade name Neoflon®, by Daikin Industries, Ltd, Japan. The polytetrafluoroethylene can be, e.g., a polymer sold in connection with the trade name Teflon®, by DuPont of Wilmington, Del. The stator generally includes a plurality of ports. The plurality of ports can be, e.g., a vent port, a pump port, and the like.

In accordance with embodiments of the present disclosure, exemplary methods of operating a rotary selector valve are provided that generally include providing a valve body that includes a rotor and a stator. The stator generally includes a first port for flow of a first flow material and a second port for flow of a second flow material. The rotor generally includes a groove for flow of at least one of the first flow material and the second flow material. The rotor generally includes a vent groove disposed between the first port and the second port for venting at least a portion of at least one of the first flow material and the second flow material to an exterior of the valve body. The exemplary methods generally include rotating the rotor relative to the stator.

The exemplary methods further include flowing a first flow material through the first port and flowing a second flow material through the second port. In addition, the exemplary methods include preventing, via the vent groove, at least one of flow of the first flow material into the second port and flow of the second flow material into the first port.

In accordance with embodiments of the present disclosure, exemplary flow systems are provided that generally include a first pressurized reservoir, a second pressurized reservoir, and a rotary selector valve. The first pressurized reservoir includes a first flow material therein. The second pressurized reservoir includes a second flow material therein. The rotary selector valve is fluidly connected to the first and second pressurized reservoirs. The rotary selector valve includes a valve body that includes a rotor and a stator. The stator includes a first port for flow of the first flow material and a second port for flow of the second flow material. The rotor includes a groove for flow of at least one of the first flow material and the second flow material. The rotor includes a vent groove disposed between the first port and the second port for venting at least a portion of at least one of the first flow material and the second flow material to an exterior of the valve body.

The exemplary flow system can be, e.g., a $CO_2$-based chromatography system. The flow system includes at least one pump for pumping at least one of the first flow material and the second flow material. The vent groove prevents at least one of flow of the first flow material into the second port and flow of the second flow material into the first port. The vent groove is configured as a C-shaped groove. The stator includes a vent port and a pump port.

The above exemplary embodiments in accordance with the present disclosure provide many advantages. For example, one or more embodiments described herein prevent leakage of $CO_2$ to the environment or to non-desired flow lines. As a result, less $CO_2$ is lost during operation, thereby providing cost savings. In addition, by preventing $CO_2$ leakage, a safer operating environment is provided as the highly pressurized $CO_2$ is prevented from entering non-desired flow lines (e.g., flow lines not designed to handle high pressures). As a result, failure created by over pressurization of methanol lines or a methanol reservoir is prevented.

Other advantages and features will become apparent from the following detailed description considered in conjunction with the accompanying drawings. It is to be understood, however, that the drawings are designed as an illustration only and not as a definition of the limits of the invention.

BRIEF DESCRIPTION OF THE DRAWINGS

To assist those of skill in the art in making and using the disclosed rotary selector valves and associated systems and methods, reference is made to the accompanying figures (which are not necessarily to scale), wherein:

FIGS. 11A-C show top, cross-sectional and detailed views of an exemplary rotor;

DESCRIPTION OF EXEMPLARY EMBODIMENTS

Figure 1:
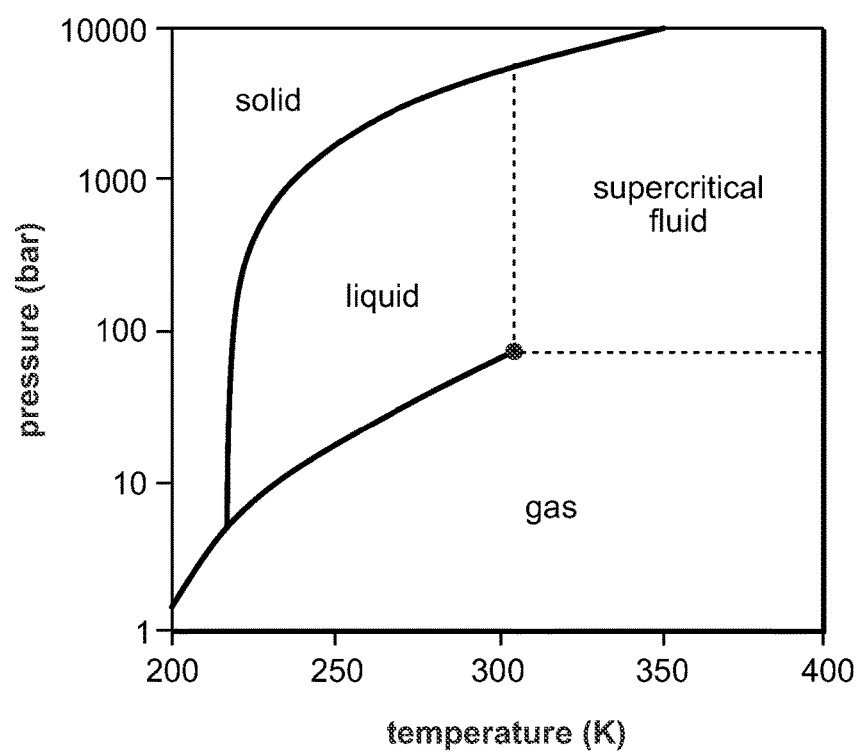
FIG. 1 is an exemplary graph of the physical state of a substance in relation to a temperature and pressure associated with the substance.

SFC or $CO_2$-based chromatography systems can be adapted as a hybrid between HPLC and GC apparatuses, where the predominant modification is replacement of either the liquid or gas mobile phase with a supercritical fluid (or near supercritical fluid) mobile phase, such as with $CO_2$. In SFC or in some $CO_2$-based chromatography systems (which utilize SFs), the mobile phase is initially pumped as a liquid or gas and is brought into the supercritical region by heating or pressurizing the mobile phase above its supercritical temperature/pressure prior to entry into a column. As the mobile phase passes through an injection valve, the sample is introduced into the supercritical stream, and the mixture is then transferred into a column. The mixture passes through the column (at supercritical or liquid state) and into the detector.

In general, the mobile phase in SFC or $CO_2$-based chromatography system processes has the ability to act both as a substance carrier (like the mobile phases in GC), and dissolve substances readily (like the solvents used in LC). In addition to generally having lower viscosities and better diffusion profiles similar to those of certain gases, the mobile phase in SFC or $CO_2$-based chromatography system processes also generally has high densities and dissolving capacities similar to those of certain liquids. For example, SFs' high densities (0.2-0.5 $gm/cm^3$) provide for their remarkable ability to dissolve large, non-volatile molecules, e.g., supercritical or near supercritical $CO_2$ readily dissolves n-alkanes, di-n-alkyl phthalates, and polycyclic and aromatic compounds. ($CO_2$ under pressures and temperatures used in chromatographic processes also possess similarly high densities and dissolving capacities). Since the diffusion of solutes in a SFC or $CO_2$-based chromatography system mobile phase is about ten times greater than that in liquids (about three times less than in gases), this results in a decrease in resistance to mass transfer in the column and allows for fast high resolution separation. Also, the solvation strength of the mobile phase in SFC or $CO_2$-based chromatography system processes is directly related to the fluid density. Thus, the solubility of solids can be easily manipulated by making slight changes in temperatures and pressures.

Another important property of the mobile phase in SFC or $CO_2$-based chromatography system processes is that it provides high resolution chromatography at much lower temperatures. For example, an analyte dissolved in $CO_2$ can be recovered by reducing the pressure and allowing the sample to evaporate under ambient laboratory conditions. This property is useful when dealing with thermally unstable analytes, such as high molecular weight biopolymers or proteins.

The combination of one or more mechanical or column changes to an SFC instrument and/or a $CO_2$-based chromatography instrument coupled with the inherent properties of chromatography itself, allows for the separation of both chiral and achiral compounds, and has become increasingly predominant in the field of preparatory separations for drug discovery and development.

As is known in the art, a $CO_2$-based chromatography system, an SFC system or a UHPLC system can be pressurized with, e.g., $CO_2$, a solvent, a combination of both, or the like, and can utilize a modifier, e.g., methanol, ethanol, and the like. A rotary selector valve having three ports, e.g., a $CO_2$ port, a center outlet stator port, a modifier port, and the like, spaced 90° apart can generally be utilized to switch between a $CO_2$ port and a modifier port. Unlike most UHPLC solvents, $CO_2$ can be both in a liquid and a gaseous state. When constrained in a liquid state, $CO_2$ can generally be maintained at approximately 900 psi. However, when in a gaseous state, $CO_2$ with a viscosity of about 0.2 cP can be challenging to prevent from leaking out of the $CO_2$-based chromatography system to the atmosphere through leak paths. A potential leak path may be the methanol port, which has a lower pressurization, i.e., approximately room atmosphere. For example, $CO_2$ in a gaseous state, a liquid state, a supercritical state, or a near-supercritical state can leak through the methanol port and pressurize the methanol glass reservoir, which is at room atmosphere, to approximately 900 psi. Glass reservoirs are typically not designed for internal pressure and may therefore explode and/or shatter, causing harm to the system and/or a user.

Exemplary embodiments of the present technology include devices and associated systems and methods which provide complete or substantially complete control of flow materials, including a vent groove for venting a flow material during potential leakage from the rotary selector valve in a $CO_2$-based chromatography system.

In accordance with embodiments of the present disclosure, exemplary rotary selector valves are provided that generally include a valve body that includes a rotor and a stator. The stator includes a first port for flow of a first flow material and a second port for flow of a second flow material. The rotor includes a groove, e.g., a port, slot, or any type of opening, for flow of at least one of the first flow material and the second flow material through at least a portion of the valve. The rotor also includes a vent groove disposed between the first port and the second port for venting at least a portion of at least one of the first flow material and the second flow material to an exterior of the valve body.

Figure 2:
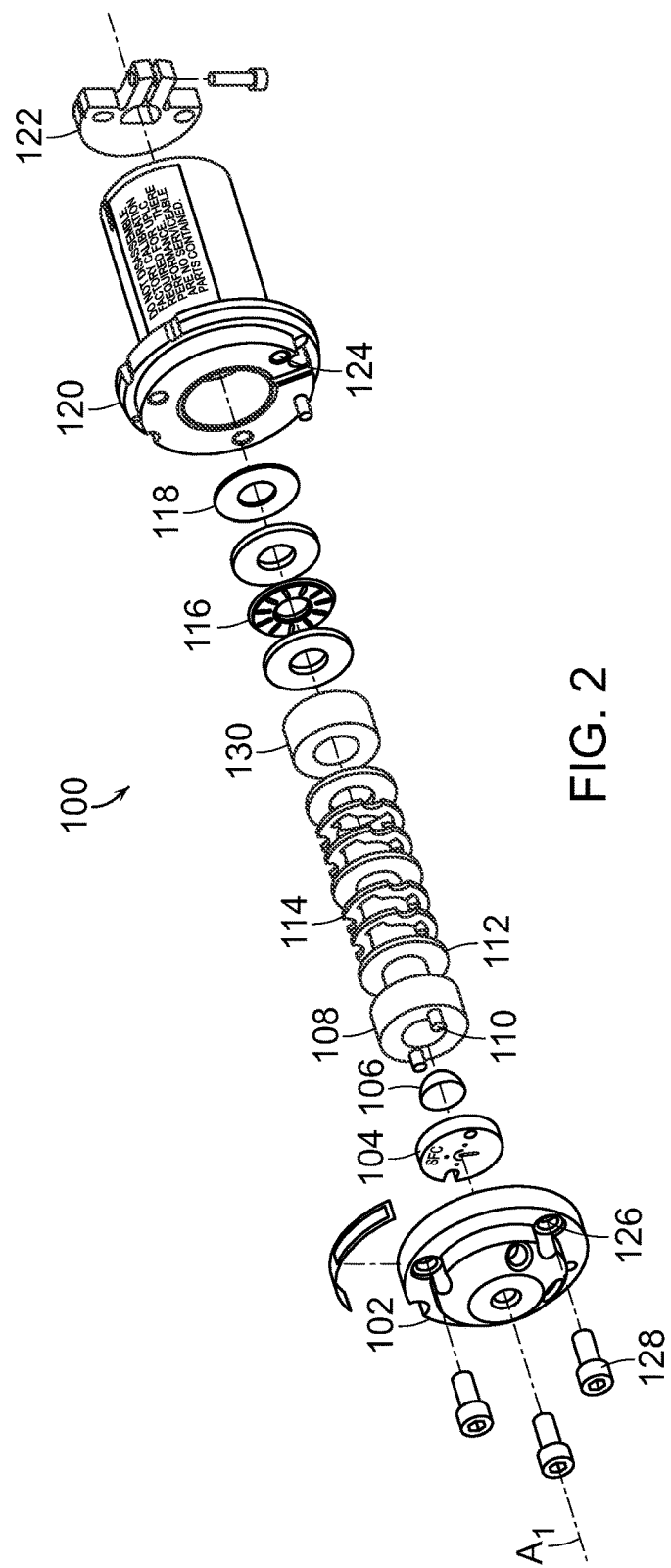
FIG. 2 shows a perspective, unassembled view of an exemplary rotary selector valve.

FIG. 2 shows a perspective, unassembled view of an exemplary rotary selector valve 100 (hereinafter "valve 100"). As shown in FIG. 2, for assembly, the components of the valve 100 discussed herein can be centrally aligned along a central axis $A_1$. The valve 100 generally includes a stator 102 and a rotor 104 in mechanical communication relative to each other. In particular, the rotor 104 rotates relative to the stator 102. The valve 100 further includes a pivot 106 which is received by shaft 108, thereby supporting the rotor 104. The shaft 108 can include pins 110 for engaging complementary apertures in the rotor 104. The shaft 108 can further receive a plurality of washers 112 and spring clover washers 114. For example, the exemplary valve 100 can include five washers 112 and four spring clover washers 114. The shaft 108 can also receive a spacer 130, a thrust bearing 116, and a shim 118. The thrust bearing 116 generally includes needle bearings and a "racetrack" or grooves on an outside surface.

Housing 120 can receive the valve 100 components discussed above and fasteners 128, e.g., hex screws, and the like, can be passed through the holes 126 and 124 to squeeze together and fixate the stator 102 to the housing 120. The holes 124 of the housing 120 can be circumferentially positioned around the central axis $A_1$. The holes 126 of the stator 102 can be circumferentially positioned around the central axis $A_1$. Flow materials, e.g., $CO_2$, and the like, can be passed through the valve 100 at a pressure of approximately 1,000 psi. Thus, the housing 120 and the stator 102 can be engaged such that the internal components are assembled and/or pressed together at a pressure range of about 1,500 to 2,000 psi, thereby exceeding the fluid pressure passing therethrough. Sufficient pressure can thereby be provided to maintain contact between the stator 102 and the rotor 104 within the housing 120. The valve 100 can further include a clamp 122, e.g., a bottom-out drive shaft clamp, which can be positioned on the outside of housing 120 and clamped around the shaft 108. The assembled components discussed above allow the stator 102 and the rotor 104 to rotate relative to each other.

Figure 3:
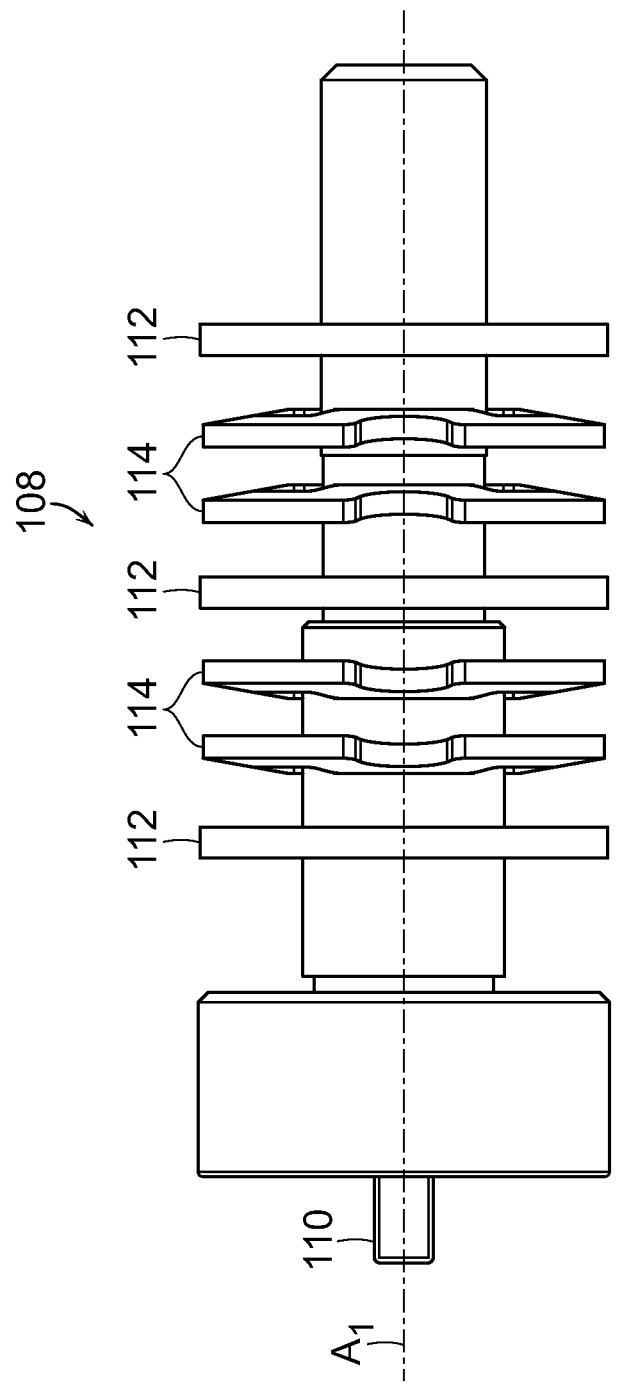
FIG. 3 shows a side view of a shaft of an exemplary rotary selector valve.

FIG. 3 shows a side view of the shaft 108, including the plurality of washers 112 and spring clover washers 114 assembled and aligned along the central axis $A_1$. In particular, FIG. 3 illustrates the positioning and/or stacking of the plurality of washers 112 and spring clover washers 114 relative to each other. The stacking order can include a first washer 112, two spring clover washers 114, a central washer 112, two additional spring clover washers 114, and an end washer 112. Each of the pairs of spring clover washers 114 should be positioned face-to-face and should be oriented such that a concave side of the spring clover washers 114 faces the central washer 112.

Figure 4A:
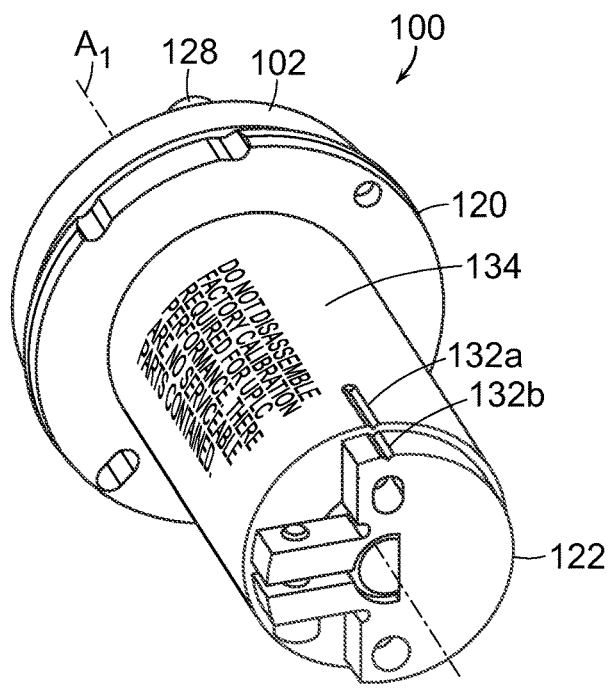
FIGS. 4A and 4B show a perspective and a detailed assembled view of an exemplary rotary selector valve.
Figure 4B:
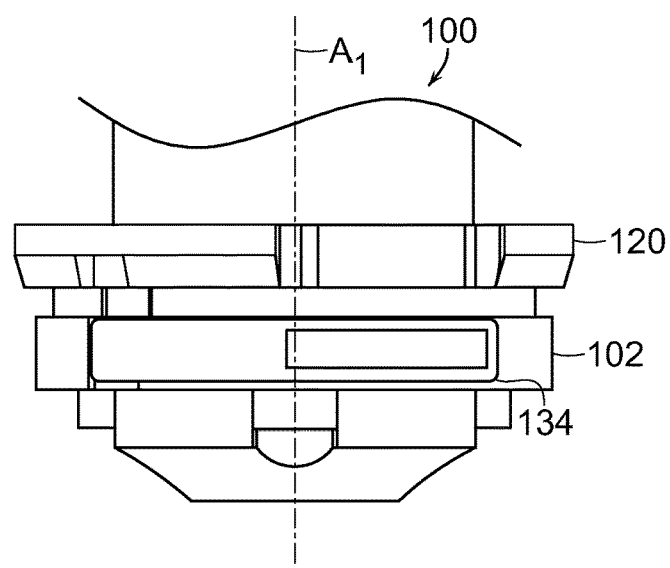

FIGS. 4A and 4B show a perspective and a detailed assembled view of an exemplary rotary selector valve. For proper functionality of the valve 100, the first and second notches 132a and 132b located on the housing 120 and the clamp 122, respectively, should be aligned during assembly. A plurality of labels 134, e.g., warning labels, instructional labels, serial numbers, and the like, can be placed on the housing 120 and/or the stator 102.

Figure 5A:
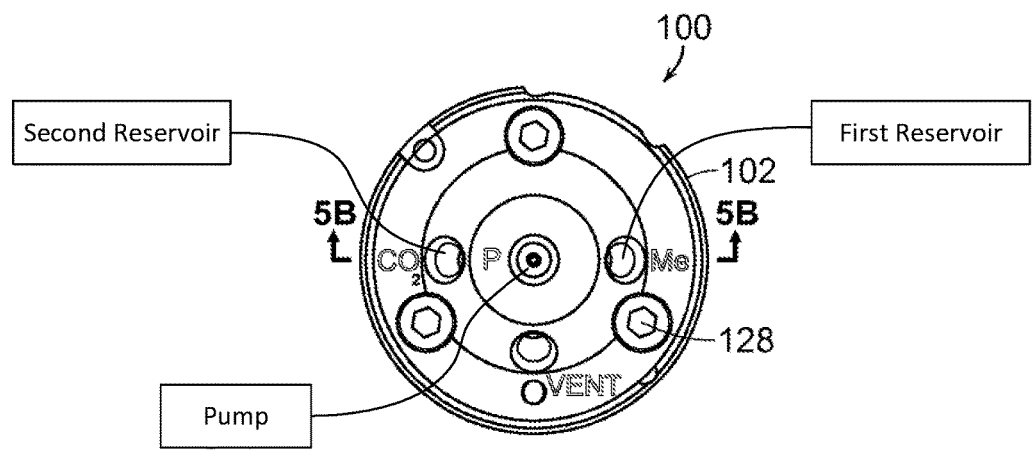
FIGS. 5A and 5B show a front and a cross-sectional assembled view of an exemplary rotary selector valve.
Figure 5B:
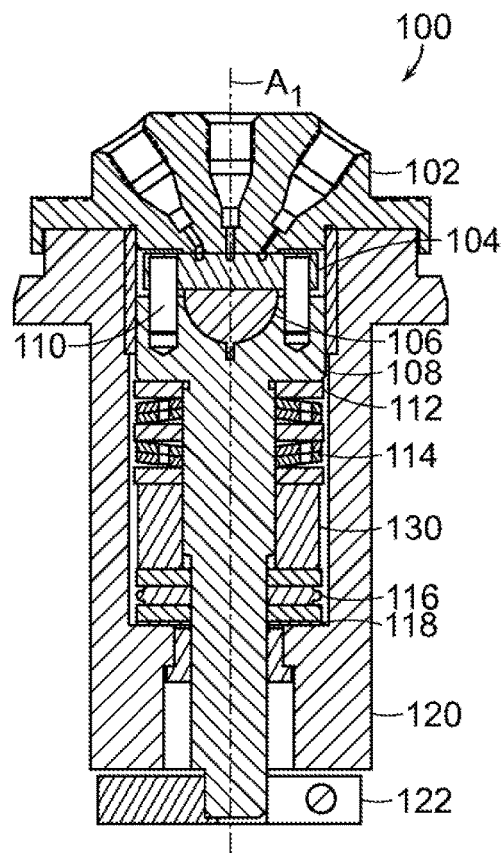
Figure 6A:
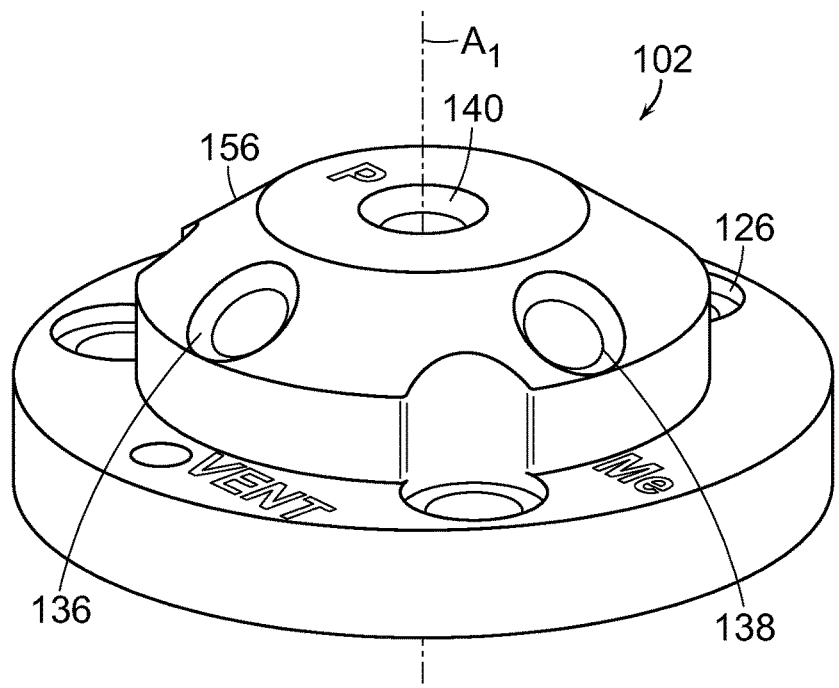
FIGS. 6A and 6B show perspective views of an exemplary stator.
Figure 6B:
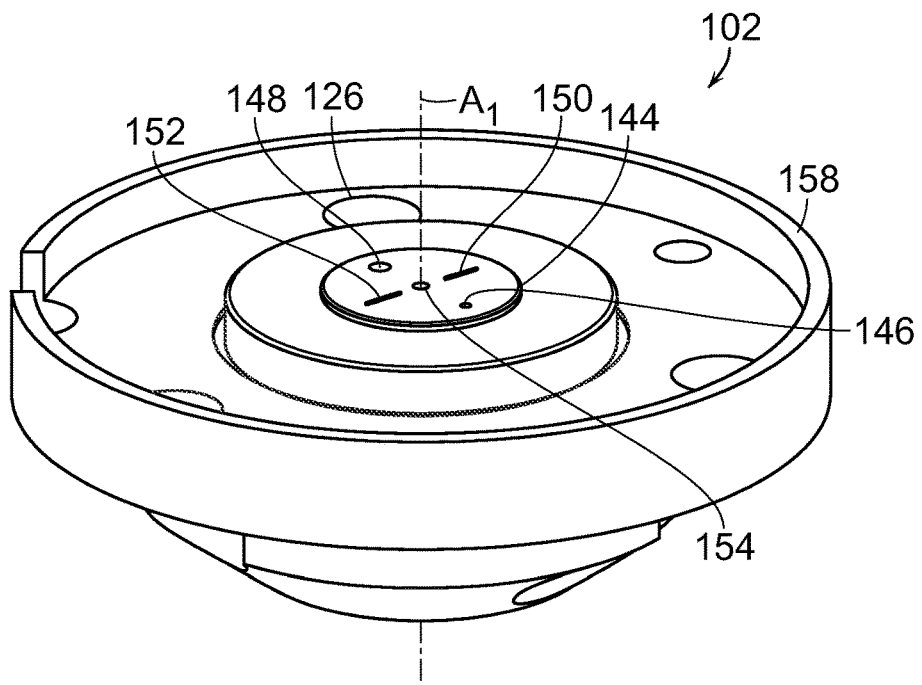
Figure 7A:
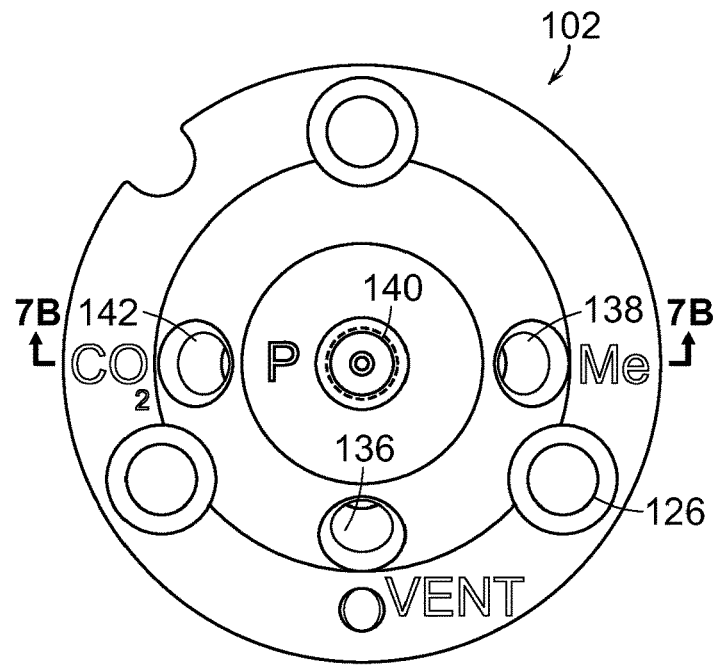
FIGS. 7A and 7B show a top and a cross-sectional view of an exemplary stator.
Figure 7B:
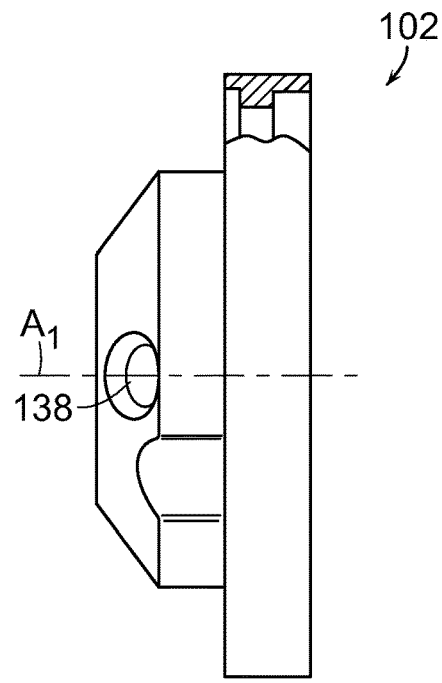

FIGS. 5A and 5B show front and cross-sectional assembled views of valve 100. The stator 102 includes a plurality of ports which will be discussed in greater detail below. As can be seen from the cross-sectional view of FIG. 5B, the internal components of valve 100 can be compactly aligned along the central axis $A_1$ and positioned relative to each other at a pressure capable of withstanding the fluidic pressure of the flow material passing therethrough. As would be understood by those of ordinary skill in the art, the positioning of the internal components maintains the valve 100 in an assembled configuration, while permitting the components to rotate relative to each other. In particular, the rotor 104 can rotate relative to the stator 102.

Turning now to FIGS. 6A-7B, views of an exemplary stator 102 are provided. The stator 102 can be fabricated from, e.g., stainless steel, and the like. For example, the material of fabrication can be 316 stainless steel with diamond-like carbon (DLC) nanofilms. The stator 102 includes a plurality of ports on a top surface 156 for flow of a variety of flow materials. The plurality of ports can be, e.g., a vent port 136, a modifier port 138, a pump port 140, a solvent port 142, and the like. The pump port 140 can be centrally positioned and aligned with the central axis $A_1$. The vent port 136, the modifier port 138 and the solvent port 142 can be circumferentially positioned around the central axis $A_1$. The modifier port 138 can be implemented for flow of a modifier, e.g., methanol, ethanol, and the like. The solvent port 142 can be implemented for flow of a solvent used for a SFC and/or $CO_2$-based chromatography system, e.g., $CO_2$, and the like. Fluidic connections can be made at the openings for the plurality of ports at the top surface 156 of the stator 102. Thus, the plurality of openings can be configured and dimensioned to receive a fluidic connection, e.g., tubing, and the like.

The openings created by the plurality of ports at the top surface 156 of the stator 102 can pass through the body of the stator 102 to the bottom surface 158. In particular, the plurality of ports result in three ports 146, 148 and 154, and two radial grooves 150 and 152 at a central panel 144. The port 154 can be centrally positioned and aligned with the central axis $A_1$. The ports 146 and 148 can be circumferentially positioned around the central axis $A_1$. The radial grooves 150 and 152 can be spaced from and can radially extend from the central axis $A_1$. The radial grooves 150 and 152 can be, e.g., ports, slots, or any type of opening. Port 146 can lead from the bottom surface 158 to the modifier port 138 at the top surface 156. Port 148 can lead from the bottom surface 158 to the solvent port 142 at the top surface 156. Port 154 can lead from the bottom surface 158 to the pump port 140 at the top surface 156. Similarly, radial groove 150 can lead from the bottom surface 158 to the vent port 136 at the top surface 156 of the stator. In some exemplary embodiments, port 146 can be about 0.01 inches in diameter. In some exemplary embodiments, ports 148 and 154 can be about 0.03 inches in diameter. In some exemplary embodiments, grooves 150 and 152 can be about 0.075 inches in length with radial ends dimensioned about 0.010 in diameter. During fabrication, the edges of the ports and grooves can be deburred to remove any burrs and/or excess material around the edges. However, the ports and grooves may be sized in accordance with a desired configuration or system requirements.

Figure 8A:
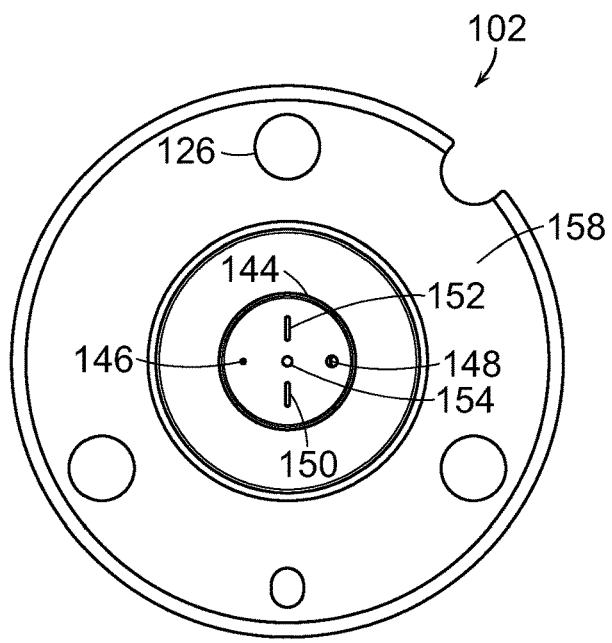
FIGS. 8A and 8B show bottom and detailed views of an exemplary stator.
Figure 8B:
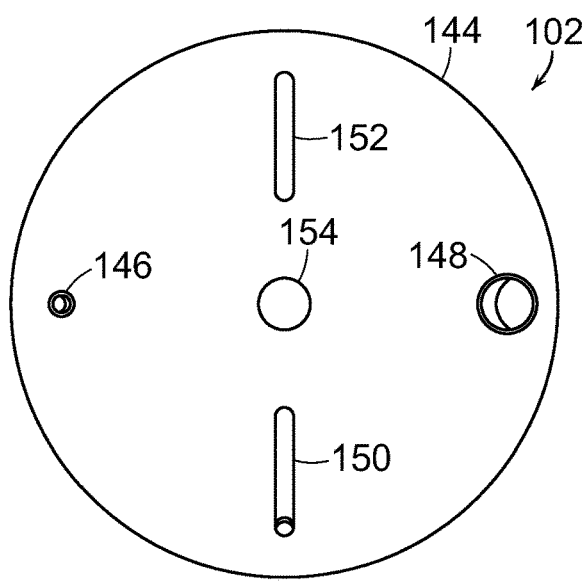

FIGS. 8A and 8B show bottom views of the stator 102, including the plurality of ports and grooves of the central panel 144. In particular, FIG. 8A shows the entire bottom surface, whereas FIG. 8B illustrates an interior portion in a magnified view. As can be seen, port 154 can be centrally positioned with respect to the circularly configured central panel 144, while ports 146 and 148 and grooves 150 and 152 can be radially positioned around port 154 at approximately 90° angles. However, the ports and grooves may be positioned in accordance with system requirements.

Figure 9A:
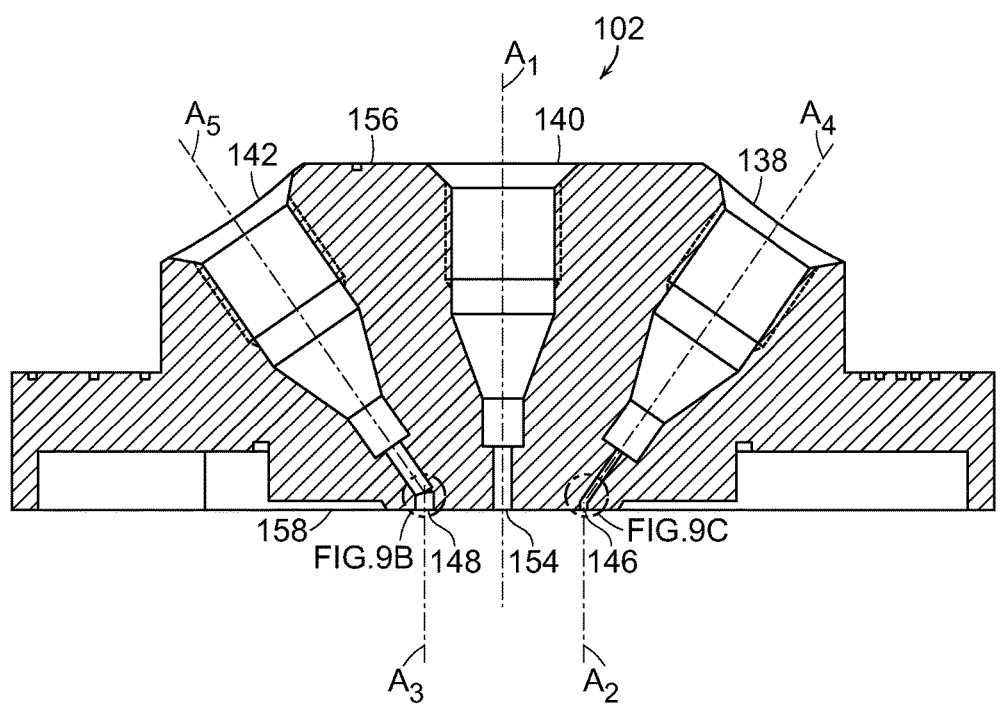
FIGS. 9A-C show cross-sectional views of an exemplary stator.
Figure 9B:
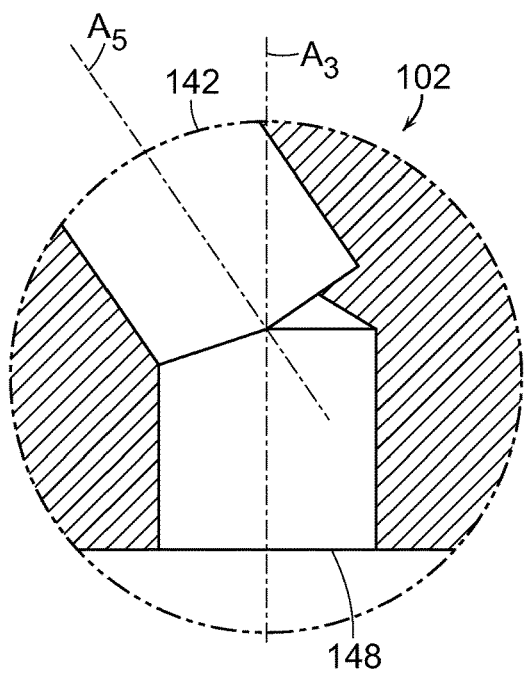
Figure 9C:
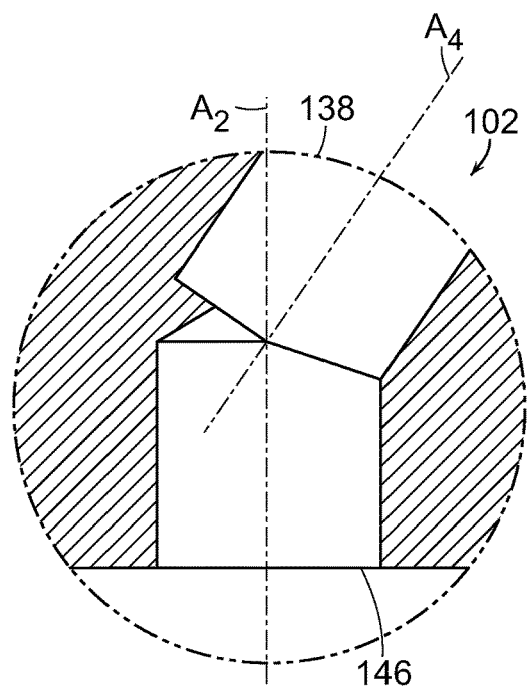

FIGS. 9A-C show cross-sectional views of the stator 102 and the internal fluidic connections between the plurality of ports. In particular, FIG. 9A illustrates three inlet ports, i.e., a solvent port 142, a pump port 140, and a modifier port 138, at the top surface 156 of the stator 102. As described above, fluidic paths and/or connections are created internally between the solvent port 142 and the port 148, the pump port 140 and the port 154, and the modifier port 138 and the port 146. FIGS. 9B and 9C show detailed cross-sectional views of the fluidic connections at the angled ports, i.e., ports 146 and 148. The pump port 140 and the port 154 can be centrally aligned along the central axis $A_1$. The port 146 can be spaced from the port 154 and can be centrally aligned along the axis $A_2$ which is parallel to the central axis $A_1$. The port 148 can be spaced from the port 154 and can be centrally aligned along the axis $A_3$ which is parallel to the central axis $A_1$. The modifier port 138 can be aligned along the axis $A_4$ which can be angled, e.g., at approximately 45°, relative to the port 146 and the axis $A_2$. The solvent port 142 can be aligned along the axis $A_5$ and can be angled, e.g., at approximately 45°, relative to the port 148 and the axis $A_3$.

Figure 10:
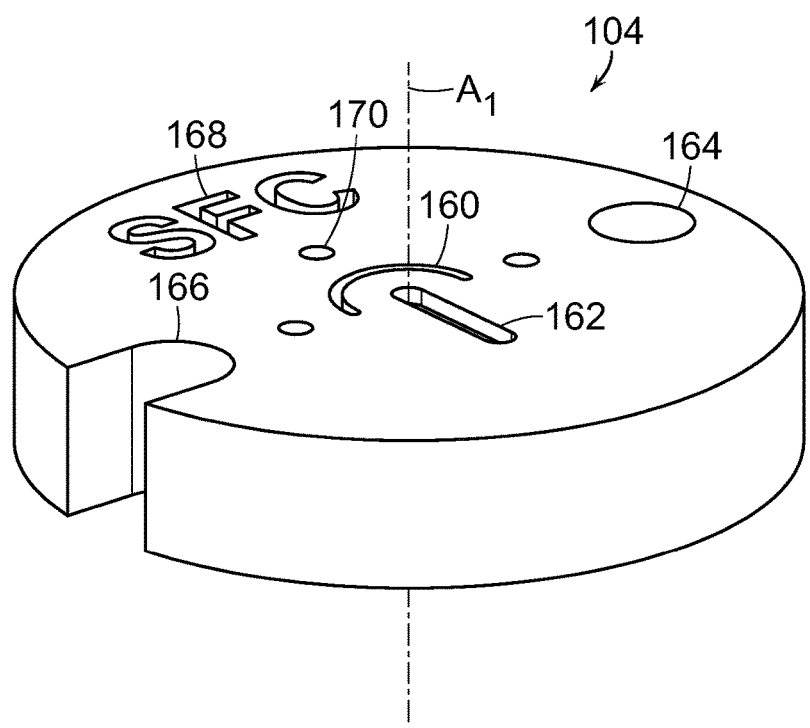
FIG. 10 shows a perspective view of an exemplary rotor.

FIG. 10 shows a perspective view of an exemplary rotor 104 of valve 100. Rotor 104 can define a substantially circular configuration and can be fabricated from, e.g., polyether ether ketone (PEEK), polytrifluorochloroethylene (PCTFE), polyimide, ultra-high-molecular-weight polyethylene (UHMWPE), polytetrafluoroethylene (PTFE), and the like. The polytrifluorochloroethylene can be, e.g., a polymer associated with U.S. registered trade name Kel-F® of 3M Corporation of St. Paul, Minn., or a polymer sold in connection with the trade name Neoflon®, by Daikin Industries, Ltd, Japan. The polytetrafluoroethylene can be, e.g., a polymer sold in connection with the trade name Teflon®, by DuPont of Wilmington, Del. The rotor 104 generally includes first and second apertures 164 and 166 configured and dimensioned to receive pins 110 of the shaft 108. The first and second apertures 164 and 166 can be circumferentially positioned relative to the central axis $A_1$. In some exemplary embodiments, the second aperture 166 can be configured as an open aperture extending along a side surface of the rotor 104. Pins 110 can be inserted into the first and second apertures 164 and 166 of the rotor 104 such that the rotor 104 and the shaft 108 rotate in unison.

The rotor 104 includes a vent groove 160, which is shown in FIG. 10 as substantially C-shaped, i.e., an approximately 180° radial extension circumferentially spaced around the central axis $A_1$. The vent groove 160 generally defines a C-shaped annular ring machined into the rotor 104 and fluidically connected to the two radial grooves 150 and 152, i.e., stator slots, which are connected to the vent port 136. In other exemplary embodiments, the vent groove 160 can have varying or different configurations than shown in FIG. 10. As will be discussed in greater detail below, the vent groove 160 generally acts as a safety path to prevent the leakage and/or interaction of flow materials passing through the valve 100. In particular, vent groove 160 allows any leaking flow materials to vent to the atmosphere, i.e., to an exterior of the valve 100 body. Although described as a groove, it should be understood that vent groove 160 can be, e.g., a port, a slot, or any type of opening. The rotor 104 further includes a radial groove 162 configured and dimensioned to create fluidic connections with flow materials passing through the valve 100. One end of the radial groove 162 can be aligned with the central axis $A_1$ and an opposing end of the radial groove 162 can radially extend from the central axis $A_1$. The rotor 104 may include dimples 170 which can be implemented for, e.g., wear purposes, and a label and/or engraving 168 of characters.

FIGS. 11A-C show top, cross-sectional and detailed views of the exemplary rotor 104. In particular, FIG. 11B shows a cross-sectional view of the rotor 104 of FIG. 11A taken along line 11B-B and FIG. 11C shows a detailed cross-sectional view of the encircled area in FIG. 11B. The vent groove depth $D_1$ can be approximately 0.01 inches into the rotor 104 and the vent groove width $W_1$ can be approximately 0.01 inches. The dimple and radial groove depth $D_2$ can be approximately 0.031 into the rotor 104 and the dimple and radial groove width $W_2$ can be approximately 0.031 inches. The length of the radial groove 162 can be approximately 0.16 inches. Moreover, the vent groove 160 can be fabricated such that a sufficient vent path is created for a flow material. During fabrication, the radial groove 162 and the vent groove 160 can be deburred to remove burrs and/or excessive materials around the groove edges. In general, $D_1$, $D_2$, $W_1$ and/or $W_2$ can be sized to accommodate system applications or requirements.

Figure 12:
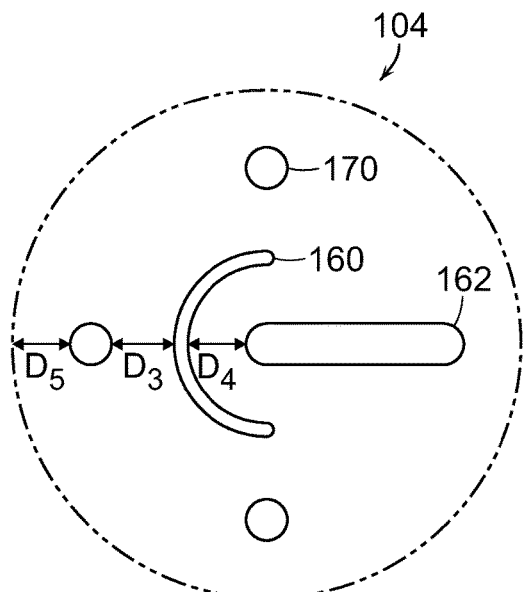
FIG. 12 shows a detailed top view of an exemplary rotor.

FIG. 12 shows a detailed top view of an exemplary rotor 104. In particular, FIG. 12 illustrates the positioning of the dimples 170, vent groove 160 and radial groove 162 relative to each other. The radial groove 162 can be positioned such that one end is at the center of the rotor 104 and aligned with the central axis $A_1$ discussed above, while the other end radially extends away from the central axis $A_1$. The dimples 170 can be radially positioned around the center of the rotor 104 at approximately 90° relative to the radial groove 162. The vent groove 160 can radially extend approximately 180° such that from a central point of the rotor 104, the vent groove 160 is positioned between the radial groove 162 and the dimples 170. Specifically, the vent groove 160 is positioned such that a safety vent path is positioned between the radial groove 162 and the dimples 170. Land sealing distances $D_3$, $D_4$, $D_5$, i.e., the distance between the vent groove 160 and the dimple 170, the distance between the vent groove 160 and the radial groove 162, and the distance between the dimple 170 and an outer edge of the rotor 104, respectively, can be in the range of approximately 0.03 to 0.05 inches. For example, the land sealing distances $D_3$, $D_4$, and $D_5$ can each be approximately 0.044 inches. In other embodiments, $D_3$, $D_4$ and $D_5$ can be spaced in accordance with system requirements. In general, $D_3$, $D_4$ and $D_5$ are not required to be equivalent or substantially equivalent. Moreover, $D_3$, $D_4$, and $D_5$ can have a greater or smaller numerical value so long as a seal is created between the rotor 104 and the stator 102 along each of the designated distances.

Figure 13A:
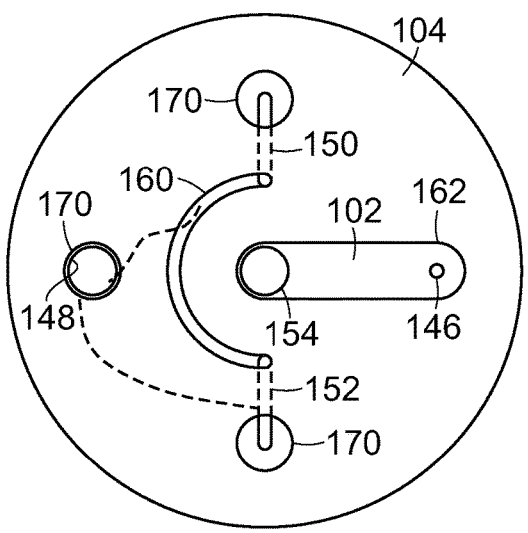
FIGS. 13A and 13B show overlay views of an exemplary rotor and stator.
Figure 13B:
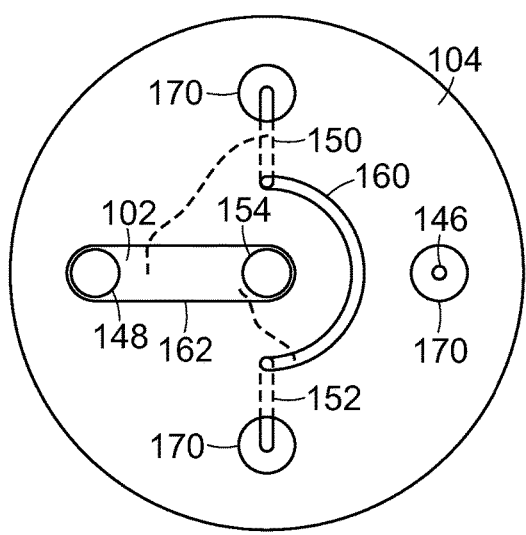

FIGS. 13A and 13B show overlay views of an exemplary rotor 104 and stator 102. In particular, as shown in FIG. 5B, the rotor 104 and stator 102 can be positioned in contact with each other such that the stator 102 can be implemented for fluidic connectivity, while the rotor 104 can be rotated relative to the stator 102 to switch between the varying flow materials, e.g., solvents, modifiers, and the like. The rotor 104 and the stator 102 can be assembled such that radial grooves 150 and 152 create fluidic paths between dimples 170 and the vent groove 160. As discussed above, the fluidic path created by radial groove 152 leads to a vent port 136. As would be understood by those of ordinary skill in the art, any flow material entering the vent groove 160 can generally be directed through the vent groove 160 to the radial groove 152 and further to the vent port 136. Thus, rather than allowing leaking flow material, if any, to escape into and/or pressurize a port in the valve 100, the leaking flow material can be redirected to the vent port 136 and vented to the atmosphere.

Still with reference to FIGS. 13A and 13B, the rotor 104 can be rotated (clockwise or counter clockwise) approximately 180° relative to the stator 102 such that the port 154 leading to the pump port 140 can be positioned within the radial groove 162 at all times. Further, rotating the rotor 104 allows switching between port 148 and port 146, i.e., ports leading to the solvent port 142 and the modifier port 138, respectively. For example, the position of the radial groove 162 in FIG. 13A creates a flow path and allows the pump port 140 to pump a modifier, e.g., methanol, from port 146. During pumping of the modifier from port 146, the vent groove 160 can be positioned substantially between ports 148 and 154. Thus, any leakage of a flow material from port 148, e.g., $CO_2$, (as indicated by the dashed lines) travels into the vent groove 160 and can be further vented through radial groove 152. In particular, the vent groove 160 prevents ports 148 and 154 from being fluidically connected by redirecting and venting any leaking flow material out of the system.

FIG. 13B shows the rotor 104 rotated approximately 180° from the position shown in FIG. 13A. In particular, by rotating the rotor 104, the radial groove 162 can be positioned such that a flow path is created between port 154 leading to the pump port 140 and port 148 leading to a solvent e.g., $CO_2$. The rotated vent groove 160 can be positioned substantially between ports 146 and 154 during pumping of the solvent. Thus, any leakage of a flow material from port 146 travels into the vent groove 160 and can be further vented through radial groove 152 to an exterior of the valve 100 body. Similarly, any leakage of a flow material from port 148, e.g., $CO_2$, (as indicated by the dashed lines) travels into the vent groove 160 and can be further vented through radial groove 152. The safety vent groove 160 thereby prevents at least one of flow of a first flow material, e.g., $CO_2$, into port 146 and flow of a second flow material, e.g., methanol, into port 148. Thus, for example, vent groove 160 prevents the flow of $CO_2$ into port 146, thereby preventing the pressurization and/or damage to the glass reservoir housing the methanol.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

The invention claimed is:

1. A flow system, comprising:
    a first pressurized reservoir including a first flow material therein,
    a second pressurized reservoir including a second flow material therein, and
    a rotary selector valve fluidly connected to the first and second pressurized reservoirs,
    wherein the rotary selector valve includes a valve body that includes a rotor and a stator,
    wherein the stator includes a first port for flow of the first flow material and a second port for flow of the second flow material,
    wherein the rotor includes a groove for flow of at least one of the first flow material and the second flow material, and
    wherein the rotor includes a vent groove disposed between the first port and the second port and extending partially around a central axis without encircling the central axis, the vent groove configured to vent at least a portion of at least one of the first flow material and the second flow material to an exterior of the valve body.

2. The system according to claim 1, wherein the flow system is a $CO_2$-based chromatography system.

3. The system according to claim 1, comprising at least one pump for pumping at least one of the first flow material and the second flow material.

4. The system according to claim 1, wherein the vent groove prevents at least one of flow of the first flow material into the second port and flow of the second flow material into the first port.

5. The system according to claim 1, wherein the vent groove is configured as a C-shaped groove.

6. The system according to claim 1, wherein the stator includes a vent port and a pump port.

7. The system according to claim 1, wherein the groove of the rotor is a radially extending groove.

8. The system according to claim 7, wherein the radially extending groove extends outward from the central axis.

9. The system according to claim 7, wherein the vent groove does not intersect with the radially extending groove.

10. The system according to claim 7, wherein the radially extending groove fluidly connects the first port to a third port located at the central axis when the rotor is in a first position.

11. The system according to claim 7, wherein the radially extending groove fluidly connects the second port to a third port located at the central axis when the rotor is in a second position.

* * * * *